United States Patent
Buettelmann et al.

(10) Patent No.: US 8,481,548 B2
(45) Date of Patent: *Jul. 9, 2013

(54) IMIDAZOLE DERIVATIVES

(75) Inventors: Bernd Buettelmann, Schopfheim (DE); Simona Maria Ceccarelli, Basel (CH); Georg Jaeschke, Basel (CH); Sabine Kolczewski, Rheinfelden (DE); Richard Hugh Philip Porter, Reinach (CH); Eric Vieira, Frenkendorf (CH)

(73) Assignee: Hoffman-La Roche Inc., Nutley, NJ (US)

( * ) Notice: Subject to any disclaimer, the term of this patent is extended or adjusted under 35 U.S.C. 154(b) by 1118 days.

This patent is subject to a terminal disclaimer.

(21) Appl. No.: 11/930,258

(22) Filed: Oct. 31, 2007

(65) Prior Publication Data

US 2008/0119489 A1      May 22, 2008

Related U.S. Application Data

(63) Continuation of application No. 10/858,969, filed on Jun. 2, 2004, now Pat. No. 7,332,510.

(30) Foreign Application Priority Data

Jun. 5, 2003   (EP) .................................... 03012200

(51) Int. Cl.
*A61K 31/4439* (2006.01)
*A61K 31/497* (2006.01)
*A61K 31/506* (2006.01)
*C07D 401/14* (2006.01)
*C07D 403/14* (2006.01)

(52) U.S. Cl.
USPC ...... 514/255.05; 514/341; 514/256; 514/269; 514/333; 544/333; 544/405; 546/272.7; 546/274.7; 546/275.1; 546/256

(58) Field of Classification Search
USPC . 546/272.7, 274.7, 275.1, 275, 256; 514/341, 514/256, 269, 333, 252.05, 255.05; 544/333, 544/405
See application file for complete search history.

(56) References Cited

U.S. PATENT DOCUMENTS

| | | | |
|---|---|---|---|
| 4,508,560 A | 4/1985 | Brunner et al. | |
| 7,091,222 B2 | 8/2006 | Buettelmann et al. | |
| 7,153,874 B2 | 12/2006 | Buettelmann et al. | |
| 7,332,510 B2 * | 2/2008 | Buettelmann et al. | ........ 514/341 |
| 2004/0259917 A1 | 12/2004 | Cosford et al. | |

FOREIGN PATENT DOCUMENTS

| | | |
|---|---|---|
| WO | WO 99/02497 A2 | 1/1999 |
| WO | WO 01/16121 A1 | 3/2001 |
| WO | WO 02/08205 A1 | 1/2002 |
| WO | WO 02/46166 A1 | 6/2002 |

OTHER PUBLICATIONS

Dorwald, Side Reactions in Organic Synthesis, 2005, Wiley: VCH Weinheim Preface, pp. 1-15 & Chapter 8, pp. 279-308.*
Buchwald et al., An Efficient Copper-Catalyzed Coupling of Aryl Halides with Imidazoles, Tetrahedron Letters, 1999, pp. 2657-2660, 40.
Cliff et al., Synthesis of 4,4'-Biimidazoles, Synthesis, Jul. 1994, pp. 681-682.
Ohira, Susumu, Methanolysis of Dimethyl (1-Diazo-2-Oxopropyl)Phosphonate and Reaction with Carbonyl Compounds, Synthetic Communications, 1989, pp. 561-564, 19(3&4).
Sonogashira et al., A Convenient Synthesis of 1-Alkynyl Ketones and 2-Alkynamides, Synthesis, Nov. 1977, pp. 777-778.
Fabrizio Gasparini et al, Neuropharmacology Pergamon Press, XP001032948, vol. 38, No. 10 pp. 1493-1503 (1999).
Will P.J.M. Spooren et al, Trends in Phrmacological Sciences, Elsevier Trends Journal, XP004247865, vol. 22, No. 7, pp. 331-337 (2001).

* cited by examiner

*Primary Examiner* — Patricia L Morris

(57) ABSTRACT

The present invention relates to imidazole derivatives of formula I

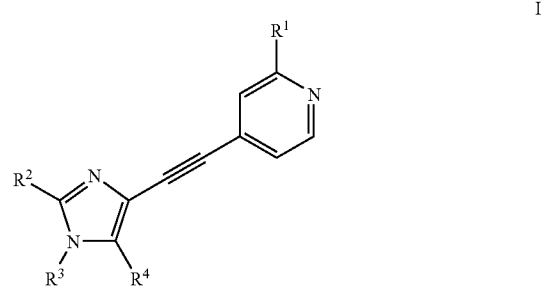

wherein $R^1$, $R^2$, $R^3$ and $R^4$ are described hereinabove. These compounds can be used in the treatment or prevention of mGluR5 receptor mediated disorders. These compounds are useful, inter alia, in the treatment or prevention of acute and/or chronic neurological disorders such as psychosis, epilepsy, schizophrenia, Alzheimer' disease, cognititve disorders and memory deficits, as well as chronic and acute pain.

18 Claims, No Drawings

IMIDAZOLE DERIVATIVES

PRIORITY TO RELATED APPLICATION(S)

This application is a [continuation of U.S. application Ser. No. 10/858,969, filed Jun. 2, 2004, now Pending; which claims the benefit of European Application No. 03012200.6, filed Jun. 5, 2003. The entire contents of the above-identified applications are hereby incorporated by reference.

FIELD OF THE INVENTION

The present invention relates to imidazole derivatives of the general formula

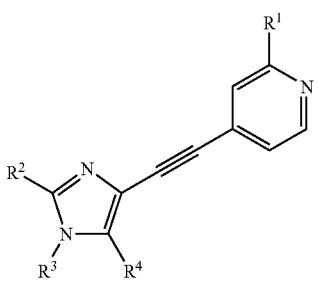

wherein $R^1$, $R^2$, $R^3$ and $R^4$ are described hereinbelow. These compounds can be used in the treatment or prevention of mGluR5 receptor mediated disorders. These compounds are useful, inter alia, in the treatment or prevention of acute and/or chronic neurological disorders such as psychosis, epilepsy, schizophrenia, Alzheimer' disease, cognititve disorders and memory deficits, as well as chronic and acute pain.

BACKGROUND OF THE INVENTION

In the central nervous system (CNS) the transmission of stimuli takes place by the interaction of a neurotransmitter, which is sent out by a neuron, with a neuroreceptor.

Glutamate is the major excitatory neurotransmitter in the brain and plays a unique role in a variety of central nervous system (CNS) functions. The glutamate-dependent stimulus receptors are divided into two main groups. The first main group, namely the ionotropic receptors, forms ligand-controlled ion channels. The metabotropic glutamate receptors (mGluR) belong to the second main group and, furthermore, belong to the family of G-protein coupled receptors.

At present, eight different members of these mGluR are known and of these some even have sub-types. According to their sequence homology, signal transduction mechanisms and agonist selectivity, these eight receptors can be sub-divided into three sub-groups:

mGluR1 and mGluR5 belong to group I; mGluR2 and mGluR3 belong to group II; and mGluR4, mGluR6, mGluR7 and mGluR8 belong to group III.

Ligands of metabotropic glutamate receptors belonging to the first group can be used for the treatment or prevention of acute and/or chronic neurological disorders such as psychosis, epilepsy, schizophrenia, Alzheimer's disease, cognitive disorders and memory deficits, as well as chronic and acute pain.

Other treatable indications in this connection are restricted brain function caused by bypass operations or transplants, poor blood supply to the brain, spinal cord injuries, head injuries, hypoxia caused by pregnancy, cardiac arrest and hypoglycaemia. Further treatable indications are ischemia, Huntington's chorea, amyotrophic lateral sclerosis (ALS), dementia caused by AIDS, eye injuries, retinopathy, idiopathic parkinsonism or parkinsonism caused by medicaments as well as conditions which lead to glutamate-deficiency functions, such as e.g. muscle spasms, convulsions, migraine, urinary incontinence, nicotine addiction, opiate addiction, anxiety, vomiting, dyskinesia and depressions.

Disorders mediated full or in part by mGluR5 are for example acute, traumatic and chronic degenerative processes of the nervous system, such as Alzheimer's disease, senile dementia, Parkinson's disease, Huntington's chorea, amyotrophic lateral sclerosis and multiple sclerosis, psychiatric diseases such as schizophrenia and anxiety, depression, pain and drug dependency (*Expert Opin. Ther. Patents* (2002), 12, (12)).

Selective mGluR5 antagonists are especially useful for the treatment of anxiety and pain.

SUMMARY OF THE INVENTION

The invention relates to a compound of formula I

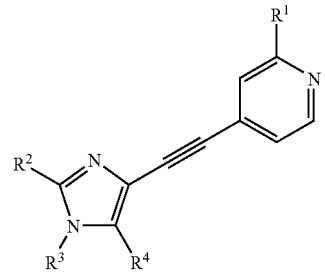

wherein
$R^1$ is halogen or cyano;
$R^2$ is lower alkyl;
$R^3$ is selected from
  aryl,
  aryl substituted by one, two or three substituents, selected from the group consisting of
    halogen,
    lower alkyl,
    cycloalkyl,
    lower alkyl-halogen,
    cyano,
    lower alkoxy,
    NR'R",
    1-morpholinyl,
    1-pyrrolidinyl,
    1-pyrrolidinyl substituted by OR or $CH_2OR$,
    piperidinyl,
    piperidinyl substituted by OR or $CH_2OR$,
    1,1-dioxo-thiomorpholinyl,
    piperazinyl, and
    piperazinyl substituted by a substituent selected from lower alkyl, cycloalkyl and $CH_2$-cycloalkyl,
  heteroaryl, and
  heteroaryl substituted by one, two or three substituents, selected from the group consisting of
    halogen,
    lower alkyl,
    cycloalkyl, lower alkyl-halogen,
cyano,
lower alkoxy,
NR'R",
1-morpholinyl,
1-pyrrolidinyl,
1-pyrrolidinyl substituted by OR or $CH_2OR$,
piperidinyl,
piperidinyl substituted by OR or $CH_2OR$,
1,1-dioxo-thiomorpholinyl,
piperazinyl, and
piperazinyl substituted by a substituent selected from lower alkyl, cycloalkyl and $CH_2$-cycloalkyl;

R is selected from the group consisting hydrogen, lower alkyl, cycloalkyl and $CH_2$-cycloalkyl;

R' and R" are each independently selected from the group hydrogen, lower alkyl, cycloalkyl, $CH_2$-cycloalkyl, and $(CH_2)_nOR$, wherein n is 1 or 2; and $R^4$ is selected from the group consisting of hydrogen, C(O)H, and $CH_2R^5$ wherein $R^5$ is selected from the group consisting of hydrogen, OH, $C_1$-$C_6$-alkyl and $C_3$-$C_{12}$-cyclo alkyl; or a pharmaceutically acceptable salt thereof.

Another embodiment of this invention is related to a process for preparing a compound according to general formula I following the general procedures as outlined above for compounds of formula I. Yet another embodiment is related to a pharmaceutical composition containing one or more compounds of the present invention and pharmaceutically acceptable excipients for the treatment and prevention of mGluR5 receptor mediated disorders, such as acute and/or chronic neurological disorders, in particular anxiety and chronic or acute pain. Yet another embodiment of this invention is related to a method of treatment and prevention of mGluR5 receptor mediated disorders as outlined above.

DETAILED DESCRIPTION OF THE INVENTION

The following definitions of general terms used in the present description apply irrespective of whether the terms in question appear alone or in combination.

The term "lower alkyl" used in the present description denotes straight-chain or branched saturated hydrocarbon residues with 1 to 6 carbon atoms, preferably with 1 to 4 carbon atoms, such as methyl, ethyl, n-propyl, i-propyl, n-butyl, t-butyl and the like.

The term "lower alkoxy" denotes a lower alkyl residue in the sense of the foregoing definition bound via an oxygen atom. Examples of "lower alkoxy" residues include methoxy, ethoxy, isopropoxy and the like.

The term "halogen" denotes fluorine, chlorine, bromine and iodine.

"Aryl" represents an aromatic carbocyclic group consisting of one individual ring, or one or more fused rings in which at least one ring is aromatic in nature. Preferred aryl group is phenyl.

The term "heteroaryl" refers to an aromatic 5- or 6-membered ring containing one or more heteroatoms selected from nitrogen, oxygen or sulfur. Preferred are those heteroaryl groups selected from nitrogen. Examples of such heteroaryl groups are pyridinyl, pyrazinyl, pyrimidinyl or pyridazinyl.

The term "cycloalkyl" denotes a saturated carbocyclic group, containing 3-12 carbon atoms, preferably 3-6 carbon atoms.

The term "pharmaceutically acceptable salt" refers to any salt derived from an inorganic or organic acid or base.

One embodiment of the present invention is related to a compound of formula I

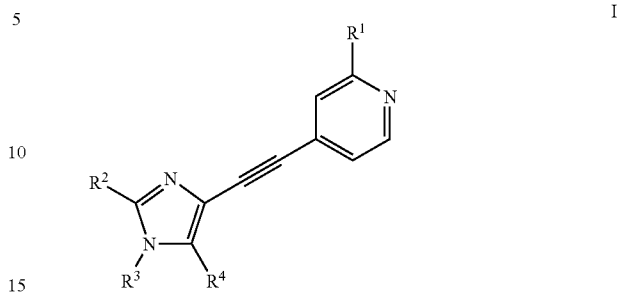

wherein
$R^1$ is halogen or cyano;
$R^2$ is lower alkyl;
$R^3$ is selected from
aryl,
aryl substituted by one, two or three substituents, selected from the group consisting of
halogen,
lower alkyl,
cycloalkyl,
lower alkyl-halogen,
cyano,
lower alkoxy,
NR'R",
1-morpholinyl,
1-pyrrolidinyl,
1-pyrrolidinyl substituted by OR or $CH_2OR$,
piperidinyl,
piperidinyl substituted by OR or $CH_2OR$,
1,1-dioxo-thiomorpholinyl,
piperazinyl, and
piperazinyl substituted by a substituent selected from lower
alkyl, cycloalkyl and $CH_2$-cycloalkyl,
heteroaryl, and
heteroaryl substituted by one, two or three substituents, selected from the group consisting of
halogen,
lower alkyl,
cycloalkyl,
lower alkyl-halogen,
cyano,
lower alkoxy,
NR'R",
1-morpholinyl,
1-pyrrolidinyl,
1-pyrrolidinyl substituted by OR or $CH_2OR$,
piperidinyl,
piperidinyl substituted by OR or $CH_2OR$,
1,1-dioxo-thiomorpholinyl,
piperazinyl, and
piperazinyl substituted by a substituent selected from lower alkyl, cycloalkyl and $CH_2$-cycloalkyl;

R is selected from the group consisting hydrogen, lower alkyl, cycloalkyl and $CH_2$-cycloalkyl;

R' and R" are each independently selected from the group hydrogen, lower alkyl, cycloalkyl, $CH_2$-cycloalkyl, and $(CH_2)_nOR$, wherein n is 1 or 2; and $R^4$ is selected from the group consisting of hydrogen, C(O)H, and $CH_2R^5$ wherein $R^5$ is selected from the group consisting of hydrogen, OH, $C_1$-$C_6$-alkyl and $C_3$-$C_{12}$-cycloalkyl; or a pharmaceutically acceptable salt thereof.

Another embodiment of the present invention is related to a compound of formula I

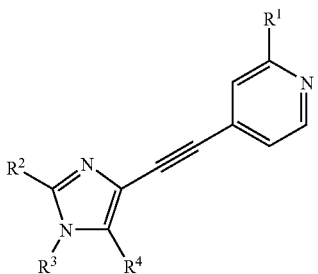

I wherein
$R^1$ is halogen;
$R^2$ is lower alkyl;
$R^3$ is selected from
  aryl substituted by one, two or three substituents, selected from the group consisting of
    halogen,
    lower alkyl,
    cycloalkyl,
    cyano, and
    lower alkoxy,
  heteroaryl, and
  heteroaryl substituted by one, two or three substituents, selected from the group consisting of
    halogen,
    lower alkyl,
    cycloalkyl,
    lower alkyl-halogen,
    cyano, and
    lower alkoxy; and
$R^4$ is selected from hydrogen and $C_1$-$C_6$-alkyl;
or a pharmaceutically acceptable salt thereof.

Encompassed in formula I is another embodiment, which is the compound of formula IA:

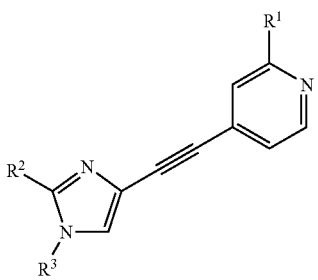

IA wherein
$R^1$ is halogen;
$R^2$ is lower alkyl;
$R^3$ is selected from the group consisting of
  aryl,
  aryl substituted by one, two or three substituents, selected from the group consisting of
    halogen,
    lower alkyl,
    cycloalkyl,
    lower alkyl-halogen,
    cyano,
    lower alkoxy,
    NR'R",
    1-morpholinyl,
    1-pyrrolidinyl,
    1-pyrrolidinyl substituted by OR or $CH_2OR$,
    piperidinyl,
    piperidinyl substituted by OR or $CH_2OR$,
    1,1-dioxo-thiomorpholinyl,
    piperazinyl, and
    piperazinyl substituted by a substituent selected from lower alkyl, cycloalkyl and $CH_2$-cycloalkyl
  heteroaryl, and
  heteroaryl substituted by one, two or three substituents selected from the group consisting of
    halogen,
    lower alkyl,
    lower alkyl-halogen,
    cyano,
    NR'R",
    1-morpholinyl,
    1-pyrrolidinyl,
    1-pyrrolidinyl substituted by OR or $CH_2OR$,
    piperidinyl,
    piperidinyl substituted by OR or $CH_2OR$,
    1,1-dioxo-thiomorpholinyl,
    piperazinyl, and
    piperazinyl substituted by a substituent selected from the group consisting of lower alkyl, cycloalkyl and $CH_2$-cycloalkyl;
R is selected from the group consisting of hydrogen, lower alkyl, cycloalkyl and $CH_2$-cycloalkyl; and
R' and R" are each independently selected from the group consisting of hydrogen, lower alkyl, cycloalkyl, $CH_2$-cycloalkyl and $(CH_2)_nOR$, where n is 1 or 2;
or a pharmaceutically acceptable salt thereof.

Yet another embodiment of this invention is directed to a compound of formula IA

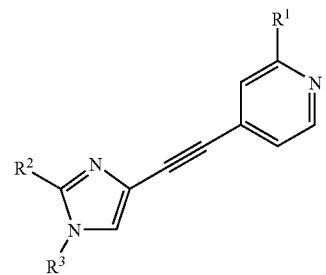

IA wherein
$R^1$ is halogen;
$R^2$ is lower alkyl; and
$R^3$ is selected from
  aryl substituted by one, two or three substituents, selected from the group consisting of
    halogen,
    lower alkyl,
    cycloalkyl,
    cyano, and
    lower alkoxy, heteroaryl, and
heteroaryl substituted by one, two or three substituents,
   selected from the group consisting of
   halogen,
   lower alkyl,
   cycloalkyl,
   lower alkyl-halogen,
   cyano, and
   lower alkoxy;
or a pharmaceutically acceptable salt thereof.

One embodiment of the compound of formula I in the present invention is where $R^1$ is halogen; $R^2$ is lower alkyl; $R^3$ is aryl substituted by one or two halogen; and $R^4$ is hydrogen.

Another embodiment of the compound of formula I in the present invention is where $R^1$ is halogen; $R^2$ is lower alkyl; $R^3$ is heteroaryl substituted by one or two lower alkyl-halogen; and $R^4$ is hydrogen.

Another embodiment of the compound of formula I in the present invention is where $R^1$ is halogen; $R^2$ is lower alkyl; $R^3$ is heteroaryl; and $R^4$ is hydrogen.

Another embodiment of the compound of formula I in the present invention is where $R^1$ is halogen; $R^2$ is lower alkyl; $R^3$ is heteroaryl substituted by one or two halogen; and $R^4$ is hydrogen.

Another embodiment of the compound of formula I in the present invention is where $R^1$ is halogen; $R^2$ is lower alkyl; $R^3$ is aryl substituted by one or two substituents selected from halogen and lower alkyl; and $R^4$ is hydrogen.

Another embodiment of the compound of formula I in the present invention is where $R^1$ is halogen; $R^2$ is lower alkyl; $R^3$ is aryl substituted by one or two lower alkyl; and $R^4$ is hydrogen.

Another embodiment of the compound of formula I in the present invention is where $R^1$ is halogen; $R^2$ is lower alkyl; $R^3$ is aryl substituted by one or two lower alkoxy; and $R^4$ is hydrogen.

Another embodiment of the compound of formula I in the present invention is where $R^1$ is halogen; $R^2$ is lower alkyl; $R^3$ is aryl substituted by one or two cyano; and $R^4$ is hydrogen.

Another embodiment of the compound of formula I in the present invention is where $R^1$ is halogen; $R^2$ is lower alkyl; $R^3$ is heteroaryl; and $R^4$ is hydrogen.

Another embodiment of the compound of formula I in the present invention is where $R^1$ is halogen; $R^2$ is lower alkyl; $R^3$ heteroaryl substituted by one or two lower alkyl; and $R^4$ is hydrogen.

Another embodiment of the compound of formula I in the present invention is where $R^1$ is halogen; $R^2$ is lower alkyl; $R^3$ is heteroaryl substituted by one or two lower alkoxy; and $R^4$ is selected from hydrogen.

Another embodiment of the compound of formula I in the present invention is where $R^1$ is cyano; $R^2$ is lower alkyl; $R^3$ is aryl substituted by one or two halogen; and $R^4$ is hydrogen.

Another embodiment of the compound of formula I in the present invention is where $R^1$ is halogen; $R^2$ is lower alkyl; $R^3$ is heteroaryl substituted by one or two substituents selected from halogen and lower alkyl; and $R^4$ is hydrogen.

Another embodiment of the compound of formula I in the present invention is where $R^1$ is cyano; $R^2$ is lower alkyl; $R^3$ is heteroaryl substituted by one or two halogen; and $R^4$ is hydrogen.

Another embodiment of the compound of formula I in the present invention is where $R^1$ is halogen; $R^2$ is lower alkyl; $R^3$ is heteroaryl substituted by one or two cycloalkyl; and $R^4$ is hydrogen.

Another embodiment of the compound of formula I in the present invention is where $R^1$ is halogen; $R^2$ is lower alkyl; $R^3$ is heteroaryl substituted by one or two substituents selected from lower alkyl-halogen and alkyl; and $R^4$ is hydrogen.

Preferred compounds of formula I and IA are those, in which $R^1$ is chloro or fluoro.

Especially preferred are those compounds from this group, in which $R^3$ is unsubstituted or substituted heteroaryl, wherein the substitution is selected from fluoro, $CF_3$ and lower alkyl, for example the following compounds:
2-[4-(2-chloro-pyridin-4-ylethynyl)-2-methyl-imidazol-1-
   yl]-4-trifluoromethyl-pyrimidine,
2-[4-(2-chloro-pyridin-4-ylethynyl)-2-methyl-imidazol-1-
   yl]-pyrazine,
2-[4-(2-chloro-pyridin-4-ylethynyl)-2-methyl-imidazol-1-
   yl]-6-trifluoromethyl-pyridine,
3-[4-(2-chloro-pyridin-4-ylethynyl)-2-methyl-imidazol-1-
   yl]-5-fluoro-pyridine,
4-[4-(2-chloro-pyridin-4-ylethynyl)-2-methyl-imidazolyl-1-
   yl]-2-trifluoromethyl-pyrimidine,
2-[4-(2-Chloro-pyridin-4-ylethynyl)-2-methyl-imidazolyl-
   1-yl]-6-methyl-4-trifluoromethyl-pyridine and
2-[4-(2-Chloro-pyridin-4-ylethynyl)-2-methyl-imidazoly-1-
   yl]-5-methyl-pyridine.

Especially preferred are further those compounds of this group, wherein $R^3$ is aryl, substituted by one or more halogen, for example the following compounds:
2-Chloro-4-[1-(4-fluoro-phenyl)-2-methyl-1H-imidazol-4-
   ylethynyl]-pyridine,
2-Fluoro-4-[1-(4-fluoro-phenyl)-2-methyl-1H-imidazol-4-
   ylethynyl]-pyridine,
2-Chloro-4-[1-(3,5-difluoro-phenyl)-2-methyl-1H-imida-
   zol-4-ylethynyl]-pyridine,
2-Chloro-4-[1-(3,5-difluoro-phenyl)-2,5-dimethyl-1H-imi-
   dazol-4-ylethynyl]-pyridine, and
2-Chloro-4-[1-(4-fluoro-phenyl)-2,5-dimethyl-1H-imida-
   zol-4-ylethynyl]-pyridine.

The compounds of formula I or IA of the invention may be prepared according to a process
which comprises reacting a compound of formula II

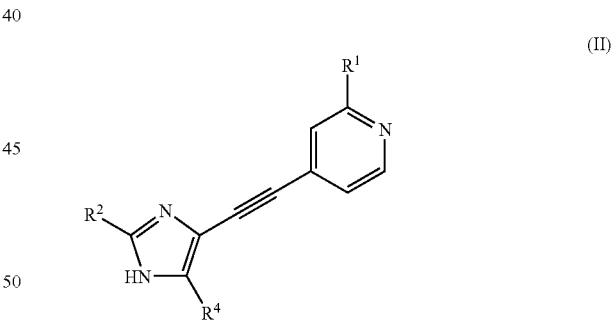

wherein $R^1$, $R^2$ and $R^4$ have the meanings as defined above, with a compound of formula III $$R^3—Z \qquad (III)$$

wherein $R^3$ has the meanings as defined above and Z is halogen or $B(OH)_2$.

The reaction as described in (a) may be carried out in accordance with standard procedures, e.g. by arylation of a compound of formula II using an aromatic boronic acid and a copper catalyst in a solvent like dichloromethane or tetrahydrofurane [see e.g. Colmann et al., Org. Lett. 2:1233 (2000)] or by heating a compound of formula II and a compound of formula III wherein Z is halogen with a base like potassium carbonate or cesium carbonate in a solvent like dimethylformamide, or Pd catalyzed according to Buchwald conditions [see e.g. Example 8; Buchwald et al., Tetrahedron Lett. 40:2657 (1999)].

In another embodiment, the compounds of formula I or IA of the invention may be prepared according to a process which comprises reacting a compound of formula IV

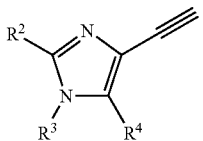

(IV)

wherein $R^2$, $R^3$ and $R^4$ have the meanings as defined above, with a compound of formula V

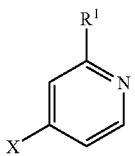

(V)

wherein $R^1$ has the meanings as defined above and X is halogen.

The reaction as described in (b) may be carried out by a Sonogashira coupling of a compound of formula IV and a compound of formula V in the presence of, e.g., CuI, $(Ph_3P)_2PdCl_2$, $Et_3N$ in a solvent like tetrahydrofuran or dimethylformamide [Sonogashira et al., Synthesis 777 (1977)]. In one embodiment the meaning X in compounds of formula V is bromine or iodine.

In yet another embodiment, the compounds of formula I or IA of the invention may be prepared according to a process which comprises reacting a compound of formula VI

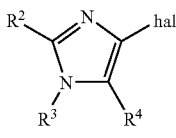

(VI)

wherein $R^2$, $R^3$ and $R^4$ have the meanings as defined above and hal is halogen, with a compound of formula VII

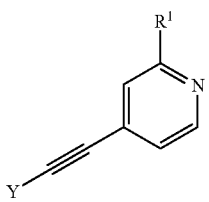

(VII)

wherein $R^1$ has the meaning as defined above and Y is trimethylsilyl or hydrogen.

The reaction described above may, e.g. be carried out in the presence of CuI, $(Ph_3P)_2PdCl_2$, $Et_3N$, n-$Bu_4F$ in a solvent like tetrahydrofuran or dimethylformamide.

If desired, the above compounds obtained may be converted into their pharmaceutically acceptable salts.

The salt forms are made by standard procedures known to the skilled artisan.

The compounds of formulae II, IV, VI and VII are novel and also an embodiment of the present invention.

The compounds of formulae III and V are commercially available or their preparation is known to the skilled artisan.

The compounds of formula II may be prepared by reacting a compound of formula VIII

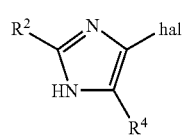

(VIII)

wherein $R^2$ and $R^4$ have the above meanings and hal is halogen, with a compound of formula VII as above.

The compounds of formula VIII may be prepared as described e.g. in Cliff and Pyne [Synthesis 681-682 (1994)].

The compounds of formula IV may be prepared by reacting a compound of formula IX

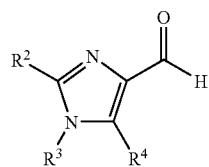

(IX)

wherein $R^2$, $R^3$ and $R^4$ have the meanings as defined above, with dimethyl (1-diazo-2-oxopropyl)phosphonate as described in Ohira [Synth. Comm. 19:561-564 (1989)].

Compounds of formula VI may be prepared by reacting a compound of formula VIII as above with a compound of formula X $$R^3-Z \qquad (X)$$

wherein $R^3$ has the meanings as defined above and Z is halogen or $B(OH)_2$.

The reaction may take place by arylation of a compound of formula VIII either by using an aromatic boronic acid (compound of formula X) and a copper catalyst in a solvent like dichloromethane or tetrahydrofurane under an oxygen atmosphere [see e.g. Colmann et al., Org. Lett. 2:1233 (2000)] or by heating with $R^3$-Z when Z is halogen with a base like potassium carbonate or cesium carbonate in a solvent like dimethylformamide, or Pd catalyzed according to Buchwald conditions [see e.g. Example 8; Buchwald et al., Tetrahedron Lett. 40:2657 (1999)].

Compounds of formula VII may be prepared by reacting a compound of formula V as above with a compound of formula XI

(XI)

The reaction may take place by a Sonogashira coupling in the presence of eg. CuI, (Ph₃P)₂PdCl₂, Et₃N in a solvent like tetrahydrofuran or dimethylformamide [Sonogashira et al., Synthesis 777 (1977)].

Compounds of formula IX may be prepared by oxidizing a compound of formula XII

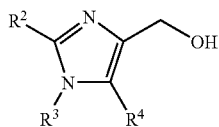

according to methods known to the skilled artisan.

Compounds of formula XII may be prepared by deprotecting a compound of formula XIII

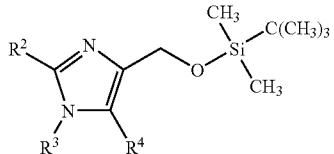

according to methods known to the skilled artisan.

Compounds of formula XIII may be prepared by alkylating a compound of formula XIV

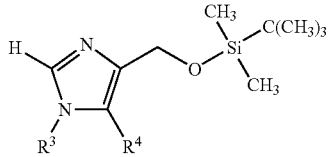

with an alkylating agent of formula XVa $R^2$-hal            (XVa)

according to methods known to the skilled artisan.

Starting compounds of formula XVa are commercially available.

Compounds of formula XIV may be prepared by treating a compound of formula XV

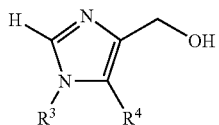

with tert.-butyl dimethyl silyl chloride according to methods known to the skilled artisan.

Compounds of formula XV may be prepared by treating a compound of formula XVI

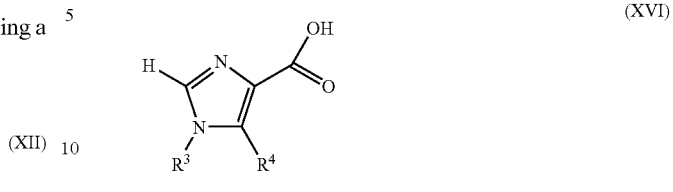

with a reducing agent according to methods known to the skilled artisan.

Compounds of formula XVI may be prepared by hydrolyzing a compound of formula XVII

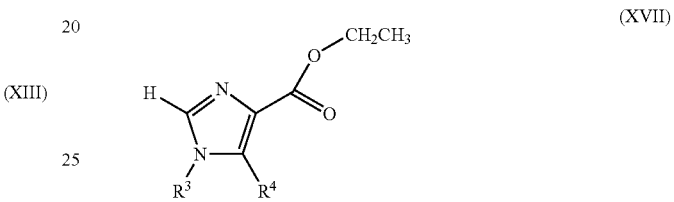

according to methods known to the skilled artisan.

Compounds of formula XVII may be prepared by treating a compound of formula XVIII $R^3$—$NH_2$            (XVIII)

with e.g. triethyl orthoformate, ethylnitro acetate, glacial acetic acid and iron powder according to methods known to the skilled artisan.

Compounds of formula XVIII are commercially available.

The compounds of general formula IA, I and their pharmaceutically acceptable salts can also be manufactured by two general procedures, which procedures are outlined below in scheme 1 for compounds wherein $R^1$ is chloro, $R^2$ is methyl and $R^3$ is 4-trifluoromethyl-pyrimidine-2-yl (see example 3), and in scheme 2 for compounds, wherein $R^1$ is chloro, $R^2$ is methyl and $R^3$ is 4-fluoro-phenyl (see example 1), but which procedures are applicable for all compounds according to formula I and IA, as described below:

a) reacting a compound of formula

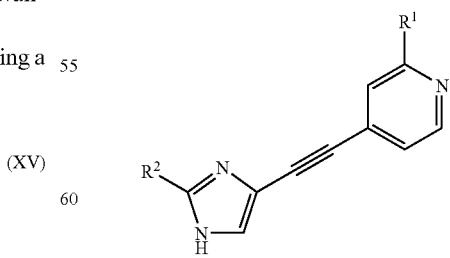

with a compound of formula $R^3Z$ III wherein $R_3$ has the meanings as defined above and Z is halogen or $B(OH)_2$, to a compound of formula

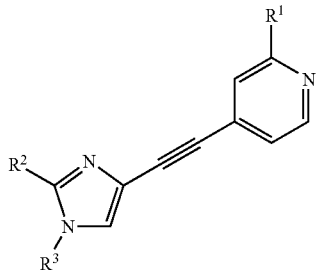

wherein R¹, R² and R³ are as described above and hal is halogen, preferably chloro or fluoro, or b) reacting a compound of formula

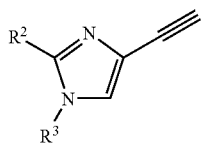

with a compound of formula

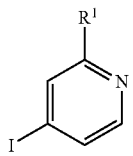

to a compound of formula

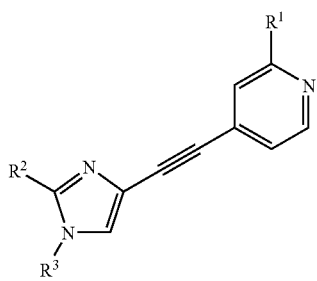

wherein R¹, R² and R³ are as described above, and if desired, when R⁴ is other than hydrogen, c) reacting the compound of formula IA with a compound of formula:

R⁴Hal          VI to a compound of formula

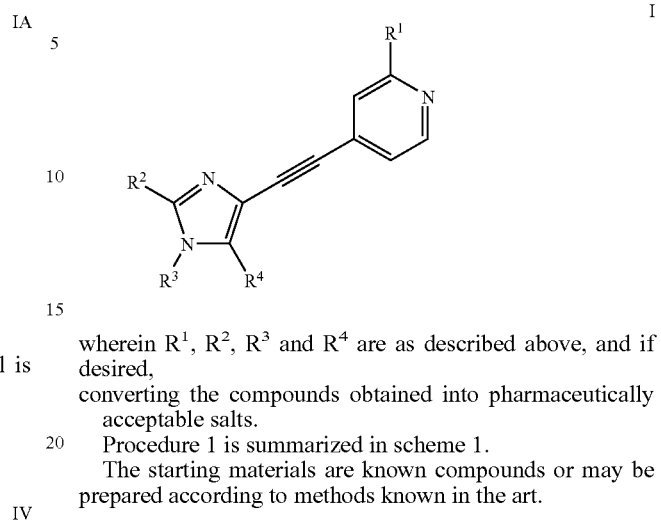

wherein R¹, R², R³ and R⁴ are as described above, and if desired,
converting the compounds obtained into pharmaceutically acceptable salts.

Procedure 1 is summarized in scheme 1.

The starting materials are known compounds or may be prepared according to methods known in the art.

Scheme 1

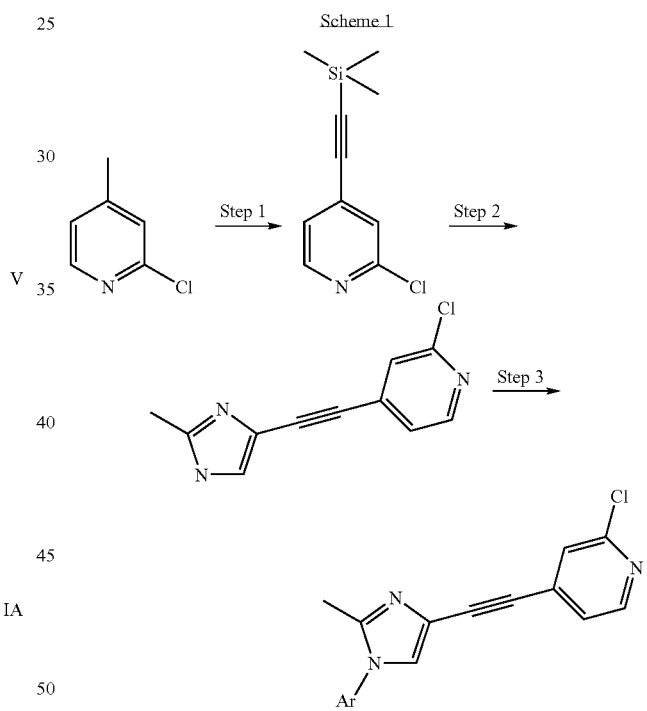

Step 1:
2-Chloro-4-iodo-pyridine is dissolved in THF and triethyl amine. Then oxygen is removed from the solution. Triphenylphosphine and bis(triphenylphosphine)palladium(II) chloride are added and the reaction mixture is stirred at room temperature for about 1 h. Copper(I) iodide and trimethylsilylacetylen are added. The reaction mixture is stirred at room temperature overnight. The desired product 2-chloro-4-trimethylsilanylethynyl-pyridine is obtained after conventional work-up. This material was used without any further purification for the next step.

Step 2:
Solution 1: 2-Chloro-4-trimethylsilanylethynyl-pyridine and 5-iodo-2-methyl-1H-imidazole, (synthesis: M. D. Cliff, S. G. Pyne, *Synthesis* 1994, 681-682) are dissolved in THF and DMF. Then oxygen is removed from the solution.

Solution 2: Triphenylphosphine, bis(triphenylphosphine)-palladium(II) chloride, copper(I) iodide and triethyl amine are dissolved in THF. Then oxygen is removed from the solution.

Solution 2 is heated to 40° C. and solution 1 is added dropwise. The reaction mixture is heated to about 60° C. and tetrabutylammonium fluoride solution is added dropwise. The reaction is then stirred at room temperature overnight. The desired product 2-chloro-4-(2-methyl-1H-imidazol-4-ylethynyl)-pyridine is obtained after conventional work-up.

Step 3:

2-Chloro-4-(2-methyl-1H-imidazol-4-ylethynyl)-pyridine is dissolved in dimethyl formamide. Potassium carbonate and 2-chloro-4-trifluoromethyl-pyrimidine are added and the reaction mixture is stirred at about 80° C. overnight. It is obtained 2-[4-(2-chloro-pyridin-4-ylethynyl)-2-methyl-imidazol-1-yl]-4-trifluoromethyl-pyrimidine.

Procedure 2 is summarized in scheme 2.

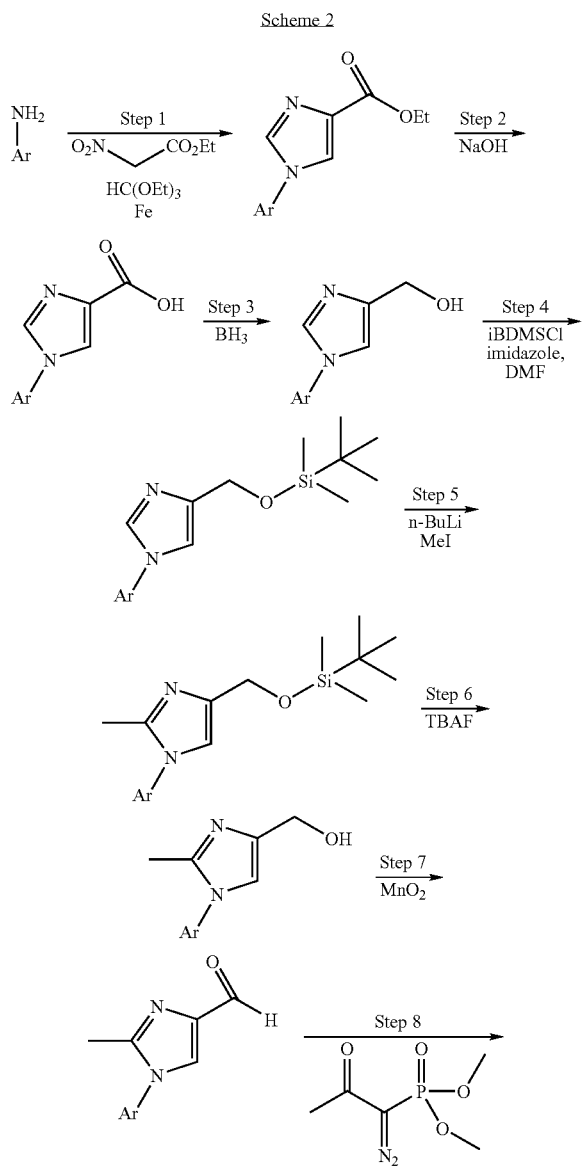

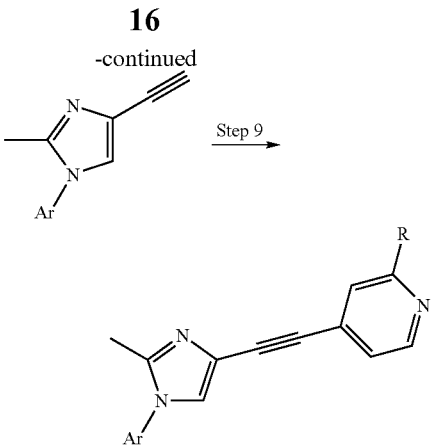

Step 1:

4-Fluoroaniline is mixed at room temperature with triethyl orthoformate, ethylnitro acetate and glacial acetic acid. The reaction mixture is refluxed with mechanical stirring for about 2 h. More triethyl orthoformate and glacial acetic acid are added. Iron powder is added in 3 portions during about 8 h while maintaining the reaction mixture at reflux. Ethyl acetate is added and reflux is continued. The crude product 1-(4-fluoro-phenyl)-1H-imidazole-4-carboxylic acid ethyl ester is used without any further purification for the next step.

Step 2:

Crude 1-(4-fluoro-phenyl)-1H-imidazole-4-carboxylic acid ethyl ester is dissolved in dioxane and sodium hydroxide solution. The reaction mixture is refluxed for about 2 h. Charcoal is added and reflux is continued. The desired compound I-(4-fluoro-phenyl)-1H-imidazole-4-carboxylic acid is obtained.

Step 3:

1-(4-Fluoro-phenyl)-1H-imidazole-4-carboxylic acid is dissolved in THF. Borane tetrahydrofuran complex in THF is added dropwise. The reaction is refluxed for 2 h and stirred at room temperature overnight. The reaction mixture is then cooled to 0° C. and methanol is added dropwise. The solvents are evaporated and the residue is taken up in HCl and refluxed for 2 h. The reaction mixture is then cooled to 0° C. and sodium hydroxide solution is added dropwise. The desired compound [1-(4-fluoro-phenyl)-1H-imidazol-4-yl]-methanol is obtained.

Step 4:

[1-(4-Fluoro-phenyl)-1H-imidazol-4-yl]-methanol is dissolved in DMF. Imidazole and tert. butyldimethyl chlorosilane are added. The reaction mixture is stirred at about 45° C. overnight. The desired compound 4-(tert-butyl-dimethyl-silanyloxymethyl)-1-(4-fluoro-phenyl)-1H-imidazole is obtained.

Step 5:

4-(tert-Butyl-dimethyl-silanyloxymethyl)-1-(4-fluoro-phenyl)-1H-imidazole is dissolved in THF and cooled to –78° C. n-Butyl lithium in hexane is added dropwise. The reaction mixture is warmed up to –25° C., kept at –25° C. for 10 min and then cooled again to –78° C. Iodomethane is added dropwise. The reaction mixture is slowly warmed up to room temperature and stirred at room temperature overnight. The desired compound 4-(tert-butyl-dimethyl-silanyloxymethyl)-1-(4-fluoro-phenyl)-2-methyl-1H-imidazole is obtained.

Step 6:

4-(tert-Butyl-dimethyl-silanyloxymethyl)-1-(4-fluoro-phenyl)-2-methyl-1H-imidazole is dissolved in THF. Tetrabutyl ammoniumfluoride in THF is added and the reaction mixture is stirred at room temperature overnight. The desired compound [1-(4-fluoro-phenyl)-2-methyl-1H-imidazol-4-yl]-methanol is obtained.

Step 7:

[1-(4-Fluoro-phenyl)-2-methyl-1H-imidazol-4-yl]-methanol is dissolved in methylene chloride. Mangan (IV) oxide is added and the reaction mixture is stirred at room temperature for 3 days. The suspension is filtered through a dicalite speed plus pad and the desired compound (4-fluoro-phenyl)-2-methyl-1H-imidazole-4-carbaldehyde is obtained.

Step 8:

Diazo-2-oxo-propyl)-phosphonic acid dimethyl ester is dissolved in methanol. Potassium carbonate is added. A solution of 1-(4-fluoro-phenyl)-2-methyl-1H-imidazole-4-carbaldehyde in methanol is added dropwise at room temperature. The reaction mixture is stirred at room temperature overnight. The desired compound 4-ethynyl-1-(4-fluoro-phenyl)-2-methyl-1H-imidazole is obtained.

Step 9:

2-Chloro-4-iodopyridine is dissolved in THF. This mixture is evacuated and backfilled with argon several times to remove oxygen from the solution. Triphenylphosphine and bis(triphenylphosphine)palladium(II) chloride are added and the reaction mixture is stirred at room temperature for 1 h. Copper(I) iodide and 4-ethynyl-1-(4-fluoro-phenyl)-2-methyl-1H-imidazole are added. The reaction mixture is stirred at room temperature for 3 days. The desired product 2-chloro-4-[1-(4-fluoro-phenyl)-2-methyl-1H-imidazol-4-ylethynyl]-pyridine is obtained.

Pharmaceutically acceptable salts of compounds of formula I can be manufactured readily according to methods known in the art and taking into consideration the nature of the compound to be converted into a salt. Inorganic or organic acids such as, for example, hydrochloric acid, hydrobromic acid, sulfuric acid, nitric acid, phosphoric acid or citric acid, formic acid, fumaric acid, maleic acid, acetic acid, succinic acid, tartaric acid, methanesulfonic acid, p-toluenesulfonic acid and the like are suitable for the formation of pharmaceutically acceptable salts of basic compounds of formula I. Compounds which contain the alkali metals or alkaline earth metals, for example sodium, potassium, calcium, magnesium or the like, basic amines or basic amino acids are suitable for the formation of pharmaceutically acceptable salts of acidic compounds.

The compounds of formula I and their pharmaceutically acceptable salts are, as already mentioned above, metabotropic glutamate receptor antagonists and can be used for the treatment or prevention of mGluR5 receptor mediated disorders, such as acute and/or chronic neurological disorders, cognitive disorders and memory deficits, as well as acute and chronic pain. Treatable neurological disorders are for instance epilepsy, schizophrenia, anxiety, acute, traumatic or chronic degenerative processes of the nervous system, such as Alzheimer's disease, senile dementia, Huntington's chorea, ALS, multiple sclerosis, dementia caused by AIDS, eye injuries, retinopathy, idiopathic parkinsonism or parkinsonism caused by medicaments as well as conditions which lead to glutamate-deficient functions, such as e.g. muscle spasms, convulsions, migraine, urinary incontinence, ethanol addiction, nicotine addiction, psychoses, opiate addiction, anxiety, vomiting, dyskinesia and depression. Other treatable indications are restricted brain function caused by bypass operations or transplants, poor blood supply to the brain, spinal cord injuries, head injuries, hypoxia caused by pregnancy, cardiac arrest and hypoglycaemia.

The compounds of formula I and their pharmaceutically acceptable salts are especially useful as analgesics. Treatable kinds of pain include inflammatory pain such as arthritis and rheumatoid disease, vasculitis, neuropathic pain such as trigeminal or herpetic neuralgia, diabetic neuropathy pain, causalgia, hyperalgesia, severe chronic pain, post-operative pain and pain associated with various conditions like cancer, angina, renal or billiay colic, menstruation, migraine and gout.

The pharmacological activity of the compounds was tested using the following method:

For binding experiments, cDNA encoding human mGlu 5a receptor was transiently transfected into EBNA cells using a procedure described by Schlaeger and Christensen [Cytotechnology 15:1-13 (1998)]. Cell membrane homogenates were stored at −80° C. until the day of assay where upon they were thawed and resuspended and polytronised in 15 mM Tris-HCl, 120 mM NaCl, 100 mM KCl, 25 mM $CaCl_2$, 25 mM $MgCl_2$ binding buffer at pH 7.4 to a final assay concentration of 20 μg protein/well.

Saturation isotherms were determined by addition of twelve [$^3$H]MPEP concentrations (0.04-100 nM) to these membranes (in a total volume of 200 μl) for 1 h at 4° C. Competition experiments were performed with a fixed concentration of [$^3$H]MPEP (2 nM) and $IC_{50}$ values of test compounds evaluated using 11 concentrations (0.3-10,000 nM). Incubations were performed for 1 h at 4° C.

At the end of the incubation, membranes were filtered onto unifilter (96-well white microplate with bonded GF/C filter preincubated 1 h in 0.1% PEI in wash buffer, Packard BioScience, Meriden, Conn.) with a Filtermate 96 harvester (Packard BioScience) and washed 3 times with cold 50 mM Tris-HCl, pH 7.4 buffer. Nonspecific binding was measured in the presence of 10 μM MPEP. The radioactivity on the filter was counted (3 min) on a Packard Top-count microplate scintillation counter with quenching correction after addition of 45 μl of microscint 40 (Canberra Packard S. A., Zürich, Switzerland) and shaking for 20 min. For functional assays, [$Ca^{2+}$]i measurements were performed as described previously by Porter et al. [Br. J. Pharmacol. 128:13-20 (1999)] on recombinant human mGlu 5a receptors in HEK-293 cells. The cells were dye loaded using Fluo 4-AM (obtainable by FLUKA, 0.2 μM final concentration). [$Ca^{2+}$]i measurements were performed using a fluorometric imaging plate reader (FLIPR, Molecular Devices Corporation, La Jolla, Calif., USA). Antagonist evaluation was performed following a 5 min preincubation with the test compounds followed by the addition of a submaximal addition of agonist.

The inhibition (antagonists) curves were fitted with a four parameter logistic equation giving $IC_{50}$, and Hill coefficient using an iterative non linear curve fitting software (Xcel fit).

For binding experiments the Ki values of the compounds tested are given. The Ki value is defined by the following formula:

$$K_i = IC_{50}/[1+L/K_d]$$

in which the $IC_{50}$ values are those concentrations of the compounds tested which cause 50% inhibition of the competing radioligand ([$^3$H]MPEP). L is the concentration of radioligand used in the binding experiment and the $K_d$ value of the radioligand is empirically determined for each batch of membranes prepared.

The compounds of the present invention are mGluR 5a receptor antagonists. The activities of compounds of formula I as measured in the assay described above are in the range of $K_i$<70 nM.

| Example | Ki (nM) |
|---------|---------|
| 2 | 23 |
| 5 | 21 |
| 6 | 63 |
| 8 | 24 |
| 10 | 44 |
| 18 | 25 |
| 20 | 15 |
| 22 | 26 |
| 25 | 40 |
| 26 | 12 |
| 28 | 23 |
| 30 | 36 |
| 31 | 69 |
| 33 | 24 |
| 35 | 39 |

The compounds of formula I and pharmaceutically acceptable salts thereof can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. However, the administration can also be effected rectally, e.g. in the form of suppositories, or parenterally, e.g. in the form of injection solutions.

The compounds of formula I and pharmaceutically acceptable salts thereof can be processed with pharmaceutically inert, inorganic or organic carriers for the production of pharmaceutical preparations. Lactose, corn starch or derivatives thereof, talc, stearic acid or its salts and the like can be used, for example, as such as carriers for tablets, coated tablets, dragées and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula I, but as a rule are not necessary. Suitable carriers for suppositories are, for example, natural or hardened oils, waxes, fats, semi-liquid or liquid polyols and the like.

In addition, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As mentioned earlier, medicaments containing a compound of formula I or pharmaceutically acceptable salts thereof and a therapeutically inert excipient are also an object of the present invention, as is a process for the production of such medicaments which comprises bringing one or more compounds of formula I or pharmaceutically acceptable salts thereof and, if desired, one or more other therapeutically valuable substances into a galenical dosage form together with one or more therapeutically inert carriers.

The dosage can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult human being weighing 70 kg accordingly lies between 0.7-1400 mg per day, preferably between 7 and 700 mg per day.

The following examples are provided to further elucidate the invention:

EXAMPLE 1

2-Chloro-4-[1-(4-fluoro-phenyl)-2-methyl-1H-imidazol-4-ylethynyl]-pyridine

2-Chloro-4-iodopyridine (1.39 g, 5.8 mmol) was dissolved in 50 mL dry THF. This mixture was evacuated and backfilled with argon several times to remove oxygen from the solution. Triphenylphosphine (39 mg, 0.15 mmol) and bis(triphenylphosphine)palladium(II) chloride (170 mg, 0.24 mmol) were added and the reaction mixture was stirred at room temperature for 1 h. Copper(I) iodide (28 mg, 0.15 mmol) and 4-ethynyl-1-(4-fluoro-phenyl)-2-methyl-1H-imidazole (970 mg, 4.84 mmol) were added. The reaction mixture was stirred at room temperature for 3 days. The solvent was evaporated. The residue was taken up in 100 mL water and extracted three times with ethyl acetate (100 mL each). The combined organic extracts were dried with magnesium sulfate, filtered and evaporated. The crude product was purified by flash chromatography on silica gel (cyclohexane/ethyl acetate/triethyl amine 1:0:0->10:10:1 gradient) and recrystallized from heptane and ethyl acetate. The desired product was obtained as a white solid (545 mg, 36%), MS: m/e=312.1 (M+H$^+$).

EXAMPLE 2

2-Fluoro-4-[1-(4-fluoro-phenyl)-2-methyl-1H-imidazol-4-ylethynyl]-pyridine

The title compound, MS: m/e=296.1 (M+H$^+$), was prepared in accordance with the general method of example 1 from 4-ethynyl-1-(4-fluoro-phenyl)-2-methyl-1H-imidazole and 2-fluoro-4-iodopyridine.

EXAMPLE 3

2-[4-(2-Chloro-pyridin-4-ylethynyl)-2-methyl-imidazol-1-yl]-4-trifluoromethyl-pyrimidine 2-Chloro-4-(2-methyl-1H-imidazol-4-ylethynyl)-pyridine (150 mg, 0.69 mmol) was dissolved in 5 mL dimethyl formamide. Potassium carbonate (190 mg, 1.37 mmol) and 2-chloro-4-trifluoromethyl-pyrimidine (189 mg, 0.66 mmol) were added and the reaction mixture was stirred at 80° C. overnight. The reaction mixture was poured into 70 mL water and extracted three times with ethyl acetate (100 mL each). The combined organic extracts were dried with sodium sulfate, filtered and evaporated. The crude product was recrystallized from diethyl ether and the desired compound was obtained as a white solid (190 mg, 76%), MS: m/e=364.1 (M+H$^+$).

EXAMPLE 4

2-[4-(2-Chloro-pyridin-4-ylethynyl)-2-methyl-imidazol-1-yl]-pyrazine

The title compound, MS: m/e=296.1 (M+H$^+$), was prepared in accordance with the general method of example 3 from 2-chloro-4-(2-methyl-1H-imidazol-4-ylethynyl)-pyridine and 2-chloropyrazine.

EXAMPLE 5

2-[4-(2-Chloro-pyridin-4-ylethynyl)-2-methyl-imidazol-1-yl]-6-trifluoromethyl-pyridine The title compound, MS: m/e=363.1.1 (M+H$^+$), was prepared in accordance with the general method of example 3 from 2-chloro-4-(2-methyl-1H-imidazol-4-ylethynyl)-pyridine and 2-fluoro-6-(trifluoromethyl)pyridine.

EXAMPLE 6

3-[4-(2-Chloro-pyridin-4-ylethynyl)-2-methyl-imidazol-1-yl]-5-fluoro-pyridine

The title compound, MS: m/e=313.1 (M+H$^+$), was prepared in accordance with the general method of example 3 from 2-chloro-4-(2-methyl-1H-imidazol-4-ylethynyl)-pyridine and 3,5-difluoro-pyridine.

EXAMPLE 7

2-Chloro-4-[1-(4-chloro-phenyl)-2-methyl-1H-imidazol-4-ylethynyl]-pyridine

2-Chloro-4-(2-methyl-1H-imidazol-4-ylethynyl)-pyridine (150 mg, 0.69 mmol) was dissolved in 30 mL dichloromethane. Powdered molecular sieves (3 A, 200 mg), 4-chlorobenzene boronic acid (216 mg, 1.38 mmol) and [Cu(OH)TMEDA]$_2$Cl$_2$ (113 mg, 0.24 mmol) were added. Oxygen was bubbled through the reaction mixture for 5 minutes and stirring was continued at room temperature overnight. The reaction mixture was filtered through a dicalite speed plus pad and washed with 50 mL dichloromethane. The filtrate was washed with 50 ml water, dried with magnesium sulfate, filtered and evaporated. The crude product was purified by flash chromatography on silica gel (heptane/ethylacetate 100:0->3:2 gradient) and by recrystallization from diisopropylether. The desired compound was obtained as a white solid (42 mg, 19%), MS: m/e 329.2 (M+H$^+$).

EXAMPLE 8

2-Chloro-4-[1-(3,4-dichloro-phenyl)-2-methyl-1H-imidazol-4-ylethynyl]-pyridine

The title compound, MS: m/e=363.7 (M+H$^+$), was prepared in accordance with the general method of example 7 from 2-chloro-4-(2-methyl-1H-imidazol-4-ylethynyl)-pyridine and 3,4-dichlorobenzene boronic acid.

EXAMPLE 9

2-Chloro-4-[1-(4-fluoro-phenyl)-2-isopropyl-1H-imidazol-4-ylethynyl]-pyridine fumarate Step 1: 1-(4-Fluoro-phenyl)-4-iodo-2-isopropyl-1H-imidazole The title compound, MS: m/e=331.1 (M+H$^+$), was prepared in accordance with the general method of example 7 from 5-iodo-2-isopropyl-1H-imidazole and 4-fluorobenzene boronic acid.

Step 2: 2-Chloro-4-[1-(4-fluoro-phenyl)-2-isopropyl-1H-imidazol-4-ylethynyl]-pyridine fumarate The title compound, MS: m/e=340.1 (M+H$^+$), was prepared in accordance with the general method of example B, step 2, from 2-chloro-4-trimethylsilanylethynyl-pyridine and 1-(4-fluoro-phenyl)-4-iodo-2-isopropyl-1H-imidazole and crystallization from methanol and 1.05 eq fumaric acid.

EXAMPLE 10

4-[1-(4-Fluoro-phenyl)-2-methyl-1H-imidazol-4-ylethynyl]-pyridine-2-carbonitrile The title compound, MS: m/e=303.1 (M+H$^+$), was prepared in accordance with the general method of example 7 from 4-(2-methyl-1H-imidazol-4-ylethynyl)-pyridine-2-carbonitrile and 4-fluorobenzene boronic acid.

4-(2-Methyl-1H-imidazol-4-ylethynyl)-pyridine-2-carbonitrile

Triphenylphosphine (126 mg, 0.48 mmol), bis(triphenylphosphine)palladium(II) chloride (1.01 g, 1.44 mmol) and triethylamine (3.65 g, 101.2 mmol) were dissolved in 40 ml of dry THF. This mixture was evacuated and backfilled with argon several times to remove oxygen from the solution. 4-iodo-2-methyl-1H-imidazole [Tetrahedron Letters 30(11), 1409 (1989)] (5.0 g, 20.8 mmol), 4-trimethylsilanylethynyl-pyridine-2-carbonitrile (4.43 g, 22.1 mmol) and copper (I) iodide (46 mg, 0.24 mmol) were added and the mixture was warmed to 60° C. A 1M solution of tetrabutylammonium fluoride (24 ml, 24.0 mmol) was added dropwise over a period of 30 min. After the addition was finished, the reaction mixture was stirred at 60° C. for another hour. The solvent was evaporated. The residue was taken up in 200 mL water and extracted three times with 200 ml of ethyl acetate. The combined organic extracts were dried with magnesium sulfate, filtered and evaporated. The crude product was purified by flash chromatography on silica gel (methanol/methylene chloride 5:95). The desired product was obtained as a light yellow solid (1.06 g, 21%). MS: m/e=208.9 (M$^+$).

4-Trimethylsilanylethynyl-pyridine-2-carbonitrile

4-Bromo-2-pyridinecarbonitrile [Cesko-Slovenska Farmacie 25(5), 181 (1976)] (0.73 g, 4.0 mmol) was dissolved in 18 mL dry THF. This mixture was evacuated and backfilled with argon several times to remove oxygen from the solution. Triphenylphosphine (31 mg, 0.12 mmol) and bis(triphenylphosphine)palladium(II) chloride (141 mg, 0.20 mmol) were added and the reaction mixture was stirred at room temperature for 1 h. Copper(I) iodide (23 mg, 0.12 mmol) and trimethylsilyl-acetylene (590 mg, 6.0 mmol) were added. The reaction mixture was stirred at room temperature for 3 days. The solvent was evaporated. The residue was taken up in 100 mL water and extracted three times with 100 ml of ethyl acetate. The combined organic extracts were dried with magnesium sulfate, filtered and evaporated. The crude product was purified by flash chromatography on silica gel (heptane/methylene chloride 1:2). The desired product was obtained as a yellow oil (329 mg, 41%), MS: m/e=201.3 (M+H$^+$).

EXAMPLE 11

2-Chloro-4-[1-(2,4-difluoro-phenyl)-2-methyl-1H-imidazol-4-ylethynyl]-pyridine

The title compound, MS: m/e=330.4 (M+H$^+$), was prepared in accordance with the general method of example 7 from 2-chloro-4-(2-methyl-1H-imidazol-4-ylethynyl)-pyridine and 2,4-difluorobenzene boronic acid.

EXAMPLE 12

2-Chloro-4-[1-(3,4-difluoro-phenyl)-2-methyl-1H-imidazol-4-ylethynyl]-pyridine

The title compound, MS: m/e=330.4 (M+H$^+$), was prepared in accordance with the general method of example 7 from 2-chloro-4-(2-methyl-1H-imidazol-4-ylethynyl)-pyridine and 3,4-difluorobenzene boronic acid.

EXAMPLE 13

4-[1-(3,4-Difluoro-phenyl)-2-methyl-1H-imidazol-4-ylethynyl]-pyridine-2-carbonitrile The title compound, MS: m/e=321.5 (M+H$^+$), was prepared in accordance with the general method of example 7 from 4-(2-Methyl-1H-imidazol-4-ylethynyl)-pyridine-2-carbonitrile and 3,4-fluorobenzene boronic acid.

EXAMPLE 14

2-Chloro-4-[1-(3-fluoro-phenyl)-2-methyl-1H-imidazol-4-ylethynyl]-pyridine

The title compound, MS: m/e=312.5 (M+H$^+$), was prepared in accordance with the general method of example 7 from 2-chloro-4-(2-methyl-1H-imidazol-4-ylethynyl)-pyridine and 3-fluorobenzene boronic acid.

EXAMPLE 15

2-Chloro-4-[1-(3,5-difluoro-phenyl)-2-methyl-1H-imidazol-4-ylethynyl]-pyridine

The title compound, MS: m/e=330.3 (M+H$^+$), was prepared in accordance with the general method of example 7 from 2-chloro-4-(2-methyl-1H-imidazol-4-ylethynyl)-pyridine and 3,5-difluorobenzene boronic acid.

EXAMPLE 16

4-[1-(3,5-Difluoro-phenyl)-2-methyl-1H-imidazol-4-ylethynyl]-pyridine-2-carbonitrile The title compound, MS: m/e=321.4 (M+H$^+$), was prepared in accordance with the general method of example 7 from 4-(2-methyl-1H-imidazol-4-ylethynyl)-pyridine-2-carbonitrile and 3,5-fluorobenzene boronic acid.

EXAMPLE 17

2-Chloro-4-[1-(3-fluoro-4-methyl-phenyl)-2-methyl-1H-imidazol-4-ylethynyl]-pyridine The title compound, MS: m/e=326.4 (M+H$^+$), was prepared in accordance with the general method of example 7 from 2-chloro-4-(2-methyl-1H-imidazol-4-ylethynyl)-pyridine and 3-fluoro-4-methyl-benzene boronic acid.

EXAMPLE 18

2-Chloro-4-[1-(4-fluoro-3-methyl-phenyl)-2-methyl-1H-imidazol-4-ylethynyl]-pyridine The title compound, MS: m/e=326.4 (M+H$^+$), was prepared in accordance with the general method of example 7 from 2-chloro-4-(2-methyl-1H-imidazol-4-ylethynyl)-pyridine and 4-fluoro-3-methyl-benzene boronic acid.

EXAMPLE 19

2-Chloro-4-[1-(3-chloro-4-fluoro-phenyl)-2-methyl-1H-imidazol-4-ylethynyl]-pyridine The title compound, MS: m/e=347.2 (M+H$^+$), was prepared in accordance with the general method of example 7 from 2-chloro-4-(2-methyl-1H-imidazol-4-ylethynyl)-pyridine and 3-chloro-4-fluoro-benzene boronic acid.

EXAMPLE 20

2-Chloro-4-[1-(4-methyl-phenyl)-2-methyl-1H-imidazol-4-ylethynyl]-pyridine

The title compound, MS: m/e=308.8 (M+H$^+$), was prepared in accordance with the general method of example 7 from 2-chloro-4-(2-methyl-1H-imidazol-4-ylethynyl)-pyridine and 4-methyl-benzene boronic acid.

EXAMPLE 21

2-Chloro-4-[1-(3-methoxy-phenyl)-2-methyl-1H-imidazol-4-ylethynyl]-pyridine

The title compound, MS: m/e=324.8 (M+H$^+$), was prepared in accordance with the general method of example 7 from 2-chloro-4-(2-methyl-1H-imidazol-4-ylethynyl)-pyridine and 3-methoxy-benzene boronic acid.

EXAMPLE 22

2-Chloro-4-[1-(4-methoxy-phenyl)-2-methyl-1H-imidazol-4-ylethynyl]-pyridine

The title compound, MS: m/e=324.8 (M+H$^+$), was prepared in accordance with the general method of example 7 from 2-chloro-4-(2-methyl-1H-imidazol-4-ylethynyl)-pyridine and 4-methoxy-benzene boronic acid.

EXAMPLE 23

3-[4-(2-Chloro-pyridin-4-ylethynyl)-2-methyl-imidazol-1-yl]-benzonitrile

The title compound, MS: m/e=319.8 (M+H$^+$), was prepared in accordance with the general method of example 7 from 2-chloro-4-(2-methyl-1H-imidazol-4-ylethynyl)-pyridine and 3-cyano-benzene boronic acid.

EXAMPLE 24

2-[4-(2-Chloro-pyridin-4-ylethynyl)-2-methyl-imidazol-1-yl]-pyrimidine

The title compound, MS: m/e=296.5 (M+H$^+$), was prepared in accordance with the general method of example 3 from 2-chloro-4-(2-methyl-1H-imidazol-4-ylethynyl)-pyridine and 2-chloro-pyrimidine.

EXAMPLE 25

2-[4-(2-Chloro-pyridin-4-ylethynyl)-2-methyl-imidazol-1-yl]-4-methyl-pyrimidine

The title compound, MS: m/e=310.4 (M+H$^+$), was prepared in accordance with the general method of example 3 from 2-chloro-4-(2-methyl-1H-imidazol-4-ylethynyl)-pyridine and 2-chloro-4-methyl-pyrimidine.

EXAMPLE 26

2-[4-(2-Chloro-pyridin-4-ylethynyl)-2-methyl-imidazol-1-yl]-4-methoxy-pyrimidine The title compound, MS: m/e=326.5 (M+H$^+$), was prepared in accordance with the general method of example 3 from 2-chloro-4-(2-methyl-1H-imidazol-4-ylethynyl)-pyridine and 2-chloro-4-methoxy-pyrimidine.

EXAMPLE 27

2-[4-(2-Chloro-pyridin-4-ylethynyl)-2-methyl-imidazol-1-yl]-5-fluoro-pyrimidine

The title compound, MS: m/e=314.5 (M+H$^+$), was prepared in accordance with the general method of example 3 from 2-chloro-4-(2-methyl-1H-imidazol-4-ylethynyl)-pyridine and 2-chloro-5-fluoro-pyrimidine.

EXAMPLE 28

4-[4-(2-Chloro-pyridin-4-ylethynyl)-2-methyl-imidazol-1-yl]-2-trifluoromethyl-pyrimidine The title compound, MS: m/e=364.5 (M+H$^+$), was prepared in accordance with the general method of example 3 from 2-chloro-4-(2-methyl-1H-imidazol-4-ylethynyl)-pyridine and 4-chloro-2-trifluoromethyl-pyrimidine.

EXAMPLE 29

2-[4-(2-Chloro-pyridin-4-ylethynyl)-2-methyl-imidazol-1-yl]-6-methyl-pyridine

The title compound, MS: m/e=309.5 (M+H$^+$), was prepared in accordance with the general method of example 3 from 2-chloro-4-(2-methyl-1H-imidazol-4-ylethynyl)-pyridine and 2-fluoro-6-methyl-pyridine.

EXAMPLE 30

2-[4-(2-Chloro-pyridin-4-ylethynyl)-2-methyl-imidazol-1-yl]-5-methyl-pyridine

The title compound, MS: m/e=309.5 (M+H$^+$), was prepared in accordance with the general method of example 3 from 2-chloro-4-(2-methyl-1H-imidazol-4-ylethynyl)-pyridine and 2-fluoro-5-methyl-pyridine.

EXAMPLE 31

4-[1-(6-Chloro-pyridin-3-yl)-2-methyl-1H-imidazol-4-ylethynyl]-pyridine-2-carbonitrile The title compound, MS: m/e=320.0, 322.1 (M+H$^+$), was prepared in accordance with the general method of example 7 from 4-(2-Methyl-1H-imidazol-4-ylethynyl)-pyridine-2-carbonitrile and 6-chloro-3-pyridinyl-boronic acid.

EXAMPLE 32

2-Chloro-4-[1-(6-chloro-pyridin-3-yl)-2-isopropyl-1H-imidazol-4-ylethynyl]-pyridine Step 1: 2-Chloro-5-(4-iodo-2-isopropyl-imidazol-1-yl)-pyridine The title compound, MS: m/e=348.4 (M+H$^+$), was prepared in accordance with the general method of example 7 from 5-iodo-2-isopropyl-1H-imidazole and 4-chloropyridine-5-boronic acid.

Step 2: 2-Chloro-4-[1-(6-chloro-pyridin-3-yl)-2-isopropyl-1H-imidazol-4-ylethynyl]-pyridine The title compound, MS: m/e=358.1 (M+H$^+$), was prepared in accordance with the general method of example B, step 2, from 2-Chloro-4-trimethylsilanylethynyl-pyridine and 2-Chloro-5-(4-iodo-2-isopropyl-imidazol-1-yl)-pyridine.

EXAMPLE 33

5-[4-(2-Chloro-pyridin-4-ylethynyl)-2-methyl-imidazol-1-yl]-2-cyclopropyl-pyridine Step 1: 2-Chloro-5-(4-iodo-2-methyl-imidazol-1-yl)-pyridine The title compound, MS: m/e=320.2 (M+H$^+$), was prepared in accordance with the general method of example 7 from 4-iodo-2-methyl-1H-imidazole and 4-chloropyridine-5-boronic acid.

Step 2: 2-Chloro-5-(2-methyl-4-trimethylsilanylethynyl-imidazol-1-yl)-pyridine

The title compound, MS: m/e=290.6 (M+H$^+$), was prepared in accordance with the general method of example B, step 1, from 2-chloro-5-(4-iodo-2-methyl-imidazol-1-yl)-pyridine and trimethylsilylacetylen.

Step 3: 2-Cyclopropyl-5-(2-methyl-4-trimethylsilanylethynyl-imidazol-1-yl)-pyridine 2-Chloro-5-(2-methyl-4-trimethylsilanylethynyl-imidazol-1-yl)-pyridine (425 mg, 1.47 mmol) were dissolved in 0.4M cyclopropylzinc chloride in THF (7.33 mL, 0.4M in THF) and tetrakis(triphenylphosphin)palladium (34 mg, 0.03 mmol) were added. The reaction mixture was refluxed for 16 hrs and poured into 50 mL sat. sodium bicarbonate solution. The mixture and extracted three times with ethyl acetate (50 mL each). The combined organic extracts were dried with magnesium sulfate, filtered and evaporated. The crude product was purified by flash chromatography on silica gel (heptane/ethyl acetate 100:0->1:1 gradient) and the desired product was obtained as a light yellow solid (395 mg, 91%), MS: m/e=296.2 (M+H$^+$).

Step 4: 2-Chloro-4-[1-(6-cyclopropyl-pyridin-3-yl)-2-isopropyl-1H-imidazol-4-ylethynyl]-pyridine The title compound, MS: m/e=335.6 (M+H$^+$), was prepared in accordance with the general method of example B, step 2, from 2-cyclopropyl-5-(2-methyl-4-trimethylsilanylethynyl-imidazol-1-yl)-pyridine and 2-chloro-4-iodo-pyridine.

EXAMPLE 34

2-Chloro-4-[1-(3,5-difluoro-4-methyl-phenyl)-2-methyl-1H-imidazol-4-ylethynyl]-pyridine 2-Chloro-4-[1-(3,5-difluoro-phenyl)-2-methyl-1H-imidazol-4-ylethynyl]-pyridine (200 mg, 0.607 mmol) was dissolved in 10 mL THF and cooled to −75° C. Lithiumdiisopropylamide (0.45 ml, 0.91 mmol) was added and the mixture stirred for 15 min at −75° C. Iodomethane (0.05 ml, 0.85 mmol) was added and stirring was continued at −75° C. for 2 hrs. The reaction mixture was quenched with sat. NaHCO$_3$—solution and extracted with water and ethyl acetate. The combined organic extracts were dried with sodium sulfate, filtered and evaporated. The crude product was purified by flash chromatography on silica gel (heptane/ethylacetate 90:10->20:80 gradient) and by recrystallization from ethyl acetate. The desired compound was obtained as a white solid (40 mg, 19%), MS: m/e=344.5 (M+H$^+$).

EXAMPLE 35

2-Chloro-4-[1-(4-fluoro-phenyl)-2,5-dimethyl-1H-imidazol-4-ylethynyl]-pyridine The title compound, MS: m/e=326.5 (M+H$^+$), was prepared in accordance with the general method of example 34 from 2-chloro-4-[1-(4-fluoro-phenyl)-2-methyl-1H-imidazol-4-ylethynyl]-pyridine.

EXAMPLE 36

2-[4-(2-Chloro-pyridin-4-ylethynyl)-2-methyl-imidazolyl-1-yl]-6-methyl-4-trifluoromethyl-pyridine

Step 1: 2-2-(4-Iodo-2-methyl-imidazol-1-yl)-6-methyl-4-trifluoromethyl-pyridine The title compound, MS: m/e=368.0 (M+H$^+$), was prepared in accordance with the general method of example 3 from 5-iodo-2-methyl-1H-imidazole and 2-chloro-6-methyl-4-(trifluoromethyl)-pyridine.

Step 2: 2-[4-(2-Chloro-pyridin-4-ylethynyl)-2-methyl-imidazol-1-yl]-6-methyl-4-trifluoromethyl-pyridine The title compound, MS: m/e=377.2 (M+H$^+$), was prepared in accordance with the general method of example B, step 2, from 2-chloro-4-trimethylsilanylethynyl-pyridine and 2-2-(4-Iodo-2-methyl-imidazol-1-yl)-6-methyl-4-trifluoromethyl-pyridine.

Synthesis Of Intermediates

EXAMPLE A

4-Ethynyl-1-(4-fluoro-phenyl)-2-methyl-1H-imidazole

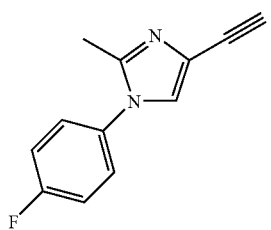

Step 1: 1-(4-Fluoro-phenyl)-1H-imidazole-4-carboxylic acid ethyl ester

4-Fluoroaniline (20.0 g, 175 mmol) was mixed at room temperature with triethyl orthoformate (35.4 g, 233 mmol), ethylnitro acetate (28.5 g, 210 mmol) and 4 mL glacial acetic acid. The reaction mixture was refluxed with mechanical stirring for 2 h. More triethyl orthoformate (200 mL) and glacial acetic acid (200 mL) were added. Iron powder (100 g, 1.79 mol) was added in 3 portions during 8 h while maintaining the reaction mixture at reflux. Ethyl acetate (700 mL) was added and reflux was continued for another 2 h. The reaction mixture was filtered through a dicalite speed plus pad and washed with 500 mL ethyl acetate. The solvents were evaporated and the crude product was used without any further purification for the next step.

Step 2: 1-(4-Fluoro-phenyl)-1H-imidazole-4-carboxylic acid

Crude 1-(4-fluoro-phenyl)-1H-imidazole-4-carboxylic acid ethyl ester (175 mmol) was dissolved in 450 mL dioxane and 450 mL 2N sodium hydroxide solution. The reaction mixture was refluxed for 2 h. Charcoal (1 g, Norit SA II) was added and reflux was continued for another 20 min. The mixture was filtered hot and washed with 50 mL 2N sodium hydroxide solution. The filtrate was treated with 550 mL 2N HCl and stirred at room temperature overnight. The solid material was filtered off and dried at 50° C. and 15 mbar. The desired compound was obtained as an off-white solid (28 g, 78%), MS: m/e 205.1 (M−H).

Step 3: [1-(4-Fluoro-phenyl)-1H-imidazol-4-yl]-methanol 1-(4-Fluoro-phenyl)-1H-imidazole-4-carboxylic acid (18 g, 87 mmol) was dissolved in 90 mL dry THF. Borane tetrahydrofuran complex (174 mL, 1M in THF, 174 mmol) was added dropwise. The reaction was refluxed for 2 h and stirred at room temperature overnight. The reaction mixture was cooled to 0° C. and 100 mL methanol were added dropwise. The solvents were evaporated. The residue was taken up in 100 mL 2N HCl and refluxed for 2 h. The reaction mixture was then cooled to 0° C. and 120 mL 2N sodium hydroxide solution were added dropwise. The solid material was filtered off and dried at 50° C. and 15 mbar. The desired compound was obtained as a white solid (13 g, 78%), MS: m/e=193.2 (M+H)$^+$.

Step 4: 4-(tert-Butyl-dimethyl-silanyloxymethyl)-1-(4-fluoro-phenyl)-1H-imidazole

[1-(4-Fluoro-phenyl)-1H-imidazol-4-yl]-methanol (13 g, 67.5 mmol) was dissolved 65 mL DMF. Imidazole (11 g, 162 mmol) and tert. butyldimethyl chlorosilane (12.2 g, 81 mmol) were added. The reaction mixture was stirred at 45° C. overnight and poured into 500 mL water. The aqueous phase was extracted three times with ethyl acetate (200 mL each). The combined organic extracts were dried with magnesium sulfate, filtered and evaporated. The crude product was purified by column chromatography on silica gel (methylene chloride/methanol 98:2) and the desired compound was obtained as a light brown oil (20 g, 96%), MS: m/e=291.2 (M-CH$_3$), m/e=249.1 (M-tert. butyl).

Step 5: 4-(tert-Butyl-dimethyl-silanyloxymethyl)-1-(4-fluoro-phenyl)-2-methyl-1H-imidazole 4-(tert-Butyl-dimethyl-silanyloxymethyl)-1-(4-fluoro-phenyl)-1H-imidazole (18.2 g, 59.2 mmol) was dissolved in 600 mL dry THF and cooled to −78° C. n-Butyl lithium (55.5 mL, 1.6M in hexane, 88.8 mmol) was added dropwise. The reaction mixture was warmed up to −25° C., kept at −25° C. for 10 min and then cooled again to −78° C. Iodomethane (7.4 mL, 11.8 mmol) was added dropwise. The reaction mixture was slowly warmed up to room temperature and stirred at room temperature overnight. The solvent was evaporated. The residue was taken up in 300 mL water and extracted three times with ethyl acetate (200 mL each). The combined organic extracts were dried with magnesium sulfate, filtered and evaporated. The crude product was purified by column chromatography on silica gel (cyclohexane/ethyl acetate 50:50->20:80 gradient) and the desired compound was obtained as an orange oil (14.7 g, 77%), MS: m/e=321.1 (M+H$^+$).

Step 6: [1-(4-Fluoro-phenyl)-2-methyl-1H-imidazol-4-yl]-methanol 4-(tert-Butyl-dimethyl-silanyloxymethyl)-1-(4-fluoro-phenyl)-2-methyl-1H-imidazole (14.7 g, 45.7 mmol) was dissolved in 200 mL THF. Tetrabutyl ammoniumfluoride (91 mL, 1M in THF, 91 mmol) was added and the reaction mixture was stirred at room temperature overnight. The solvent was evaporated. The residue was taken up in 200 mL water and extracted three times with ethyl acetate (200 mL each). The combined organic extracts were dried with magnesium sulfate, filtered and evaporated. The crude product was suspended in 150 mL ethyl acetate, filtered and dried. The desired compound was obtained as a white solid (7.16 g, 76%), MS: m/e=207.1 (M+H$^+$).

Step 7: 1-(4-Fluoro-phenyl)-2-methyl-1H-imidazole-4-carbaldehyde

[1-(4-Fluoro-phenyl)-2-methyl-1H-imidazol-4-yl]-methanol (7.16 g, 34.7 mmol) was dissolved in 2.3 L methylene chloride. Mangan (IV) oxid (26.8 g, 278 mmol) was added and the reaction mixture was stirred at room temperature for 3 days. The suspension was filtered through a dicalite speed plus pad and washed with 1 L methylene chloride. The solvents were evaporated and the desired compound was obtained as a white solid (5.87 g, 83%), MS: m/e=205.1 (M+H$^+$).

Step 8: 4-Ethynyl-1-(4-fluoro-phenyl)-2-methyl-1H-imidazole

Diazo-2-oxo-propyl)-phosphonic acid dimethyl ester (6.51 g, 33.9 mmol) was dissolved in 100 mL methanol. Potassium carbonate (7.81 g, 56.5 mmol) was added. A solution of 1-(4-fluoro-phenyl)-2-methyl-1H-imidazole-4-carbaldehyde (5.77 g, 45 mmol) in 100 mmol methanol was added dropwise at room temperature. The reaction mixture was stirred at room temperature overnight. The solvent was evaporated. The residue was taken up in 150 mL water and extracted three times with ethyl acetate (150 mL each). The combined organic extracts were dried with sodium sulfate, filtered and evaporated. The crude product was purified by flash chromatography on silica gel (heptane/ethyl acetate 100:0->0:100 gradient) and the desired compound was obtained as a white solid (3.81 g, 67%), MS: m/e=200.1 (M$^+$).

EXAMPLE B

2-Chloro-4-(2-methyl-1H-imidazol-4-ylethynyl)-pyridine

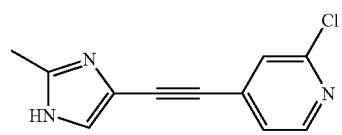

Step 1: 2-Chloro-4-trimethylsilanylethynyl-pyridine

2-Chloro-4-iodo-pyridine (10.0 g, 41.8 mmol) was dissolved in 200 mL dry THF and 17.5 mL triethyl amine. This mixture was evacuated and backfilled with argon several times to remove oxygen from the solution. Triphenylphosphine (329 mg, 1.25 mmol) and bis(triphenylphosphine)palladium(II) chloride (1.47 g, 2.09 mmol) were added and the reaction mixture was stirred at room temperature for 1 h. Copper(I) iodide (239 mg, 1.25 mmol) and trimethylsilylacetylen (6.28 g, 6.39 mmol) were added. The reaction mixture was stirred at room temperature overnight. The solvent was evaporated. The residue was taken up in 500 mL water and extracted three times with ethyl acetate (500 mL each). The combined organic extracts were dried with magnesium sulfate, filtered and evaporated. The crude product was purified by chromatography on silica gel (cyclohexane/ethyl acetate 80:20). The desired product was obtained as a light brown semi solid (10 g, >100%). This material was used without any further purification for the next step.

Step 2: 2-Chloro-4-(2-methyl-1H-imidazol-4-ylethynyl)-pyridine

Solution 1: 2-Chloro-4-trimethylsilanylethynyl-pyridine (8.9 g, purity <100% as indicated in step 1) and 5-iodo-2-methyl-1H-imidazole (13.24 g, 64 mmol, synthesis: M. D. Cliff, S. G. Pyne, *Synthesis* 1994, 681-682) were dissolved in 75 mL dry THF and 20 mL dry DMF. This mixture was evacuated and backfilled with argon several times to remove oxygen from the solution.

Solution 2: Triphenylphosphine (223 mg, 0.85 mmol), bis(triphenylphosphine)-palladium(II) chloride (1.79 g, 2.55 mmol), copper(I) iodide (81 mg, 0.43 mmol) and triethyl amine (8.87 mL, 64 mmol) were dissolved in 75 mL dry THF. This mixture was also evacuated and backfilled with argon several times to remove oxygen from the solution Solution 2 was heated to 40° C. and solution 1 was added dropwise. The reaction mixture was heated to 60° C. and tetrabutylammonium fluoride solution (1M in THF, 55 mL, 55 mmol) was added dropwise during 45 min. The reaction was than stirred at room temperature overnight. The solvent was evaporated. The residue was taken up in 200 mL water and extracted three times with ethyl acetate (200 mL each). The combined organic extracts were dried with magnesium sulfate, filtered and evaporated. The crude product was purified by chromatography on silica gel (methylene chloride/methanol 95:5)

and recrystallized from a mixture of methylene chloride and ethyl acetate. The desired product was obtained as a light brown solid (2.89 g, 31%).

EXAMPLE C

4-Chloro-2-trifluoromethyl-pyrimidine

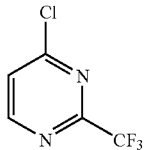

This compound was prepared according to S. Inoue, A. J. Saggiomo, E. A. Nodiff, J. Org. Chem. 1961, 26, 4504.
Preparation of the Pharmaceutical Compositions:

EXAMPLE I

Tablets of the following composition are produced in a conventional manner:

|  | mg/Tablet |
| --- | --- |
| Active ingredient | 100 |
| Powdered. lactose | 95 |
| White corn starch | 35 |
| Polyvinylpyrrolidone | 8 |
| Na carboxymethylstarch | 10 |
| Magnesium stearate | 2 |
| Tablet weight | 250 |

EXAMPLE II

Tablets of the following composition are produced in a conventional manner:

|  | mg/Tablet |
| --- | --- |
| Active ingredient | 200 |
| Powdered. lactose | 100 |
| White corn starch | 64 |
| Polyvinylpyrrolidone | 12 |
| Na carboxymethylstarch | 20 |
| Magnesium stearate | 4 |
| Tablet weight | 400 |

EXAMPLE III

Capsules of the following composition are produced:

|  | mg/Capsule |
| --- | --- |
| Active ingredient | 50 |
| Crystalline. lactose | 60 |
| Microcrystalline cellulose | 34 |
| Talc | 5 |
| Magnesium stearate | 1 |
| Capsule fill weight | 150 |

The active ingredient having a suitable particle size, the crystalline lactose and the microcrystalline cellulose are homogeneously mixed with one another, sieved and thereafter talc and magnesium stearate are admixed. The final mixture is filled into hard gelatine capsules of suitable size.

The invention claimed is:
1. A compound of formula I

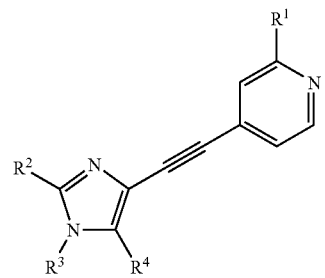

wherein
$R^1$ is halogen or cyano;
$R^2$ is lower alkyl;
$R^3$ is pyridinyl, pyrimidinyl, or pyrazinyl each of which is optionally substituted by one, two or three substituted, selected from the group consisting of
halogen,
lower alkyl,
cycloalkyl,
lower alkyl-halogen,
cyano,
lower alkoxy, and
NR'R",
R is selected from the group consisting of hydrogen, lower alkyl, cycloalkyl and $CH_2$-cycloalkyl;
R' and R" are each independently selected from the group consisting of hydrogen, lower alkyl, cycloalkyl, $CH_2$-cycloalkyl, and $(CH_2)_n OR$, wherein n is 1 or 2; and
$R^4$ is selected from the group consisting of hydrogen, C(O)H, and $CH_2R^5$ wherein $R^5$ is selected from the group consisting of hydrogen, OH, $C_1$-$C_6$-alkyl and $C_3$-$C_{12}$-cycloalkyl;
or a pharmaceutically acceptable at thereof.
2. A compound according to claim 1 wherein
$R^1$ is halogen;
$R^3$ is pyridinyl, pyrimidinyl, or pyrazinyl each of which is optionally substituted by one, two or three substituents, selected from the group consisting of
halogen,
lower alkyl,
cycloalkyl,
lower alkyl-halogen,
cyano, and
lower alkoxy, and
$R^4$ is selected from hydrogen and $C_1$-$C_6$-alkyl
or a pharmaceutically acceptable salt thereof.

3. A compound according to claim 1 wherein

R$^1$ is halogen; and

R$^4$ is hydrogen or a pharmaceutically acceptable salt thereof.

4. A compound according to claim 3 wherein

R$^3$ is pyridinyl, pyrimidinyl, or pyrazinyl each of which is optionally substituted by one, two or three substituents, selected from the group consisting of halogen, lower alkyl, cycloalkyl, cyano, and lower alkoxy or a pharmaceutically acceptable salt thereof.

5. The compound according to claim 1 wherein R$^1$ is chloro or fluoro.

6. The compound according to claim 5, wherein R$^3$ is pyridinyl, pyrimidinyl, or pyrazinyl each of which is optionally substituted with a substituent is selected from fluoro, CF$_3$ and lower alkyl.

7. The compound according to claim 6, wherein the compound is selected from the group consisting of:

2-[4-(2-chloro-pyridin-4-ylethynyl)-2-methyl-imidazol-1-yl]-4-trifluorormethyl-pyrimidine, 2-[4-(2-chloro-pyridin-4-ylethynyl)-2-methyl-imidazol-1-1-yl]-pyrazine, 2-[4-(2-chloro-pyridin-4-ylethynyl)-2-methyl-imidazol-1-yl]-6-trifluoromethyl-pyridine, 3-[4-(2-chloro-pyridin-4- ylethynyl)-2-methyl-imidazol-1-yl]-5-fluoro-pyridine, 4-[4-(2-chloro-pyridin-4-ylethynyl)-2-methyl-imidazolyl-1-yl]-2-trifluoromethyl-pyrimidine, 2-[4-(2-Chloro-pyridin-4-ylethynyl)-2-methyl-imidazolyl-1-yl]-6-methyl-4-triflueromethyl-pyrimidine, 2-[4-(2-Chloro-pyridin-4-ylethynyl)-2-methyl-imidazolyl-1-yl]-5-methyl-pyridine, and or a pharmaceutically-acceptable salt hereof.

8. Amended A process for preparing a compound of formula I (I)

which process comprises reacting a compound of formula II (II)

with a compound of formula III

R$^3$—Z  (III)

wherein

R$^1$ is halogen or cyano;

R$^2$ is lower alkyl;

R$^3$ is pyridinyl, pyrimidinyl, or pyrazinyl each of which is optionally substituted by one, two or three substituents, selected from the group consisting of halogen, lower alkyl, cycloalkyl, lower alkyl-halogen, cyano, lower alkoxy, and

NR'R",

R is selected from the group consisting of hydrogen, lower alkyl, cycloalkyl and CH$_2$-cycloalkyl;

R' and R" are each independently selected from the group consisting of hydrogen, lower alkyl, cycloalkyl, CH$_2$-cycloalkyl, and (CH$_2$)$_n$OR, wherein n is 1 or 2;

R$^4$ is selected from the group consisting of hydrogen, C(O)H, and CH$_2$R$^5$ wherein R$^5$ is selected from the group consisting of hydrogen, OH, C$_1$-C$_6$-alkyl and C$_3$-C$_{12}$-cyclo-alkyl;

and Z is halogen or B(OH)$_2$.

9. A process for preparing a compound of formula I

I which process comprises reacting a compound of formula IV (IV)

with a compound of formula V

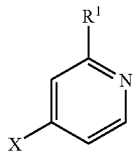

(V)

wherein

R¹ is halogen or cyano;

R² is lower alkyl;

R³ is pyridinyl, pyrazinyl, pyrimidinyl, or pyrazinyl each of which is optionally substituted by one, two or three substituents, selected from the group consisting of halogen, lower alkyl, cycloalkyl, lower alkyl-halogen cyano lower alkoxy, and

NR'R",

R is selected from the group consisting of hydrogen, lower alkyl, cycloalkyl and CH₂-cycloalkyl;

R' and R" are each independently selected from the group consisting of hydrogen, lower alkyl, cycloalkyl, CH₂-cycloalkyl, and (CH₂)ₙOR, wherein n is 1 or 2;

R⁴ is selected from the group consisting of hydrogen, C(O)H, and CH₂R⁵ wherein R⁵ is selected from the group consisting of hydrogen, OH, C₁-C₆-alkyl and C₃-C₁₂-cyclo alkyl;

and X is halogen.

10. A process of preparing a compound of formula I

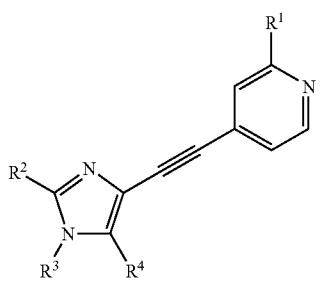

I which process comprises reacting a compound formula VI

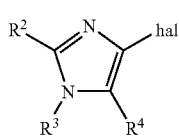

(VI)

with a compound of formula VII

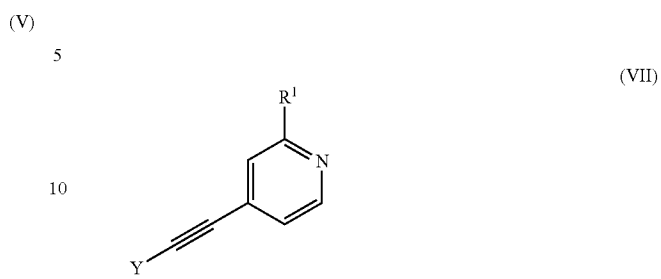

(VII)

wherein,

R¹ is halogen or cyano;

R² is lower alkyl;

R³ is pyridinyl, pyrimidinyl, or pyrazinyl each of which is optionally substituted by one, two or three substituents, selected from the group consisting of halogen, lower alkyl, cycloalkyl, lower alkyl-halogen, cyano, lower alkoxy, and

NR'R",

R is selected from the group consisting of hydrogen, lower alkyl, cycloalkyl and CH₂-cycloalkyl;

R' and R" are each independently selected from the group consisting of hydrogen, lower alkyl, cycloalkyl, CH₂-cycloalkyl, and (CH₂)ₙOR, wherein n is 1 or 2;

R⁴ is selected from the group consisting of hydrogen, C(O)H, and CH₂R⁵ wherein R⁵ is selected from the group consisting of hydrogen, OH, C₁-C₆-alkyl and C₃-C₁₂-cyclo alkyl, and Y and hal are halogen.

11. A process according to claim 8 wherein R⁴ is hydrogen.

12. A process according to claim 9 wherein R⁴ is hydrogen and X is iodide.

13. The process of claim 8 further comprising converting the compound obtained into a pharmaceutically acceptable salt.

14. The process of claim 9 further comprising converting the compound obtained into a pharmaceutically acceptable salt.

15. The process of claim 10 further comprising converting the compound obtained into a pharmaceutically acceptable salt.

16. The process of claim 11 further comprising converting the compound obtained into a pharmaceutically acceptable salt.

17. The process of claim 12 further comprising converting the compound obtained into a pharmaceutically acceptable salt.

18. A pharmaceutical composition which comprises:
(A) a compound of formula I

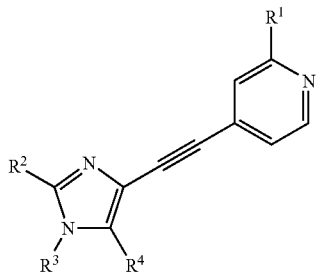

wherein
R$^1$ is halogen or cyano;
R$^2$ is lower alkyl;
R$^3$ is pyridinyl, pyrimidinyl, or pyrazinyl each of which is optionally substituted by one, two or three substituents, selected from the group consisting of
halogen,
lower alkyl,
cycloalkyl,
lower alkyl-halogen,
cyano,
lower alkoxy, and
NR'R",
R is selected from the group consisting of hydrogen, lower alkyl, cycloalkyl and CH$_2$-cycloalkyl;
R' and R" are each independently selected from the group consisting of hydrogen, lower alkyl, cycloalkyl, CH$_2$-cycloalkyl, and (CH$_2$)$_n$OR, wherein n is 1 or 2; and
R$^4$ is selected from the group consisting of hydrogen, C(O)H, and CH$_2$R$^5$ wherein R$^5$ is selected from the group consisting of hydrogen, OH, C$_1$-C$_6$-alkyl and C$_3$-C$_{12}$-cycloalkyl;
or pharmaceutically acceptable salt thereof; and
(B) a pharmaceutically-inert carrier.

* * * * *